United States Patent [19]

Beaver et al.

[11] Patent Number: 5,004,847
[45] Date of Patent: Apr. 2, 1991

[54] RECOVERY OF HEXABROMOCYCLODODECANE PARTICLES

[75] Inventors: Phillip R. Beaver, Baton Rouge, La.; Peter M. DiGiacinto, Seabrook, Tex.; Donald O. Hutchinson; Julio J. Vega, both of Baton Rouge, La.

[73] Assignee: Ethyl Corporation, Richmond, Va.

[21] Appl. No.: 457,960

[22] Filed: Dec. 27, 1989

[51] Int. Cl.$^5$ .............................................. C07C 23/02
[52] U.S. Cl. ..................................... 570/186; 570/213
[58] Field of Search ............... 570/246, 186, 211, 213, 570/216

[56] References Cited

U.S. PATENT DOCUMENTS

| | | | |
|---|---|---|---|
| 3,652,688 | 3/1972 | Olechowski et al. | 570/246 |
| 3,833,675 | 9/1974 | Newcombe et al. | 570/246 |
| 4,783,563 | 11/1988 | Tanicuchi et al. | 570/246 |
| 4,918,253 | 4/1990 | Hermolin et al. | 570/246 |

FOREIGN PATENT DOCUMENTS

| | | | |
|---|---|---|---|
| 0181414 | 5/1986 | European Pat. Off. | 570/186 |
| 3447631 | 7/1986 | Fed. Rep. of Germany | 570/186 |
| 2205830 | 12/1988 | United Kingdom | 570/186 |

*Primary Examiner*—Werren B. Lone
*Attorney, Agent, or Firm*—Terry B. Morris; David E. LaRose

[57] ABSTRACT

Methods for purifying and agglomerating hexabromocyclododecane particles by heating an admixture formed with wetcake and water.

24 Claims, No Drawings

RECOVERY OF HEXABROMOCYCLODODECANE PARTICLES

This invention relates to the manufacture of hexabromocyclododecane.

BACKGROUND

Methods of bromination of cyclododecatriene in solvent(s) to produce hexabromocyclododecane ("HBCD" hereinafter) particles are known. For example, see U.S. Pat. No. 3,558,727 (Jenkner et al). After the bromination reaction, the reaction mass can be subjected to separation techniques (e.g. filtration, centrifugation or decantation) to produce a recovered mass, e.g. wetcake, which is predominantly HBCD particles but which can additionally contain contaminants to this product, e.g. residual bromides such as hydrogen bromide and elemental or ionic bromine, dodecyl halides such as tetrabromocyclododecane, and solvents. For example, see U.S. Pat. No. 3,558,727 (Jenkner et al) and UK No. 2,205,830 (Hermolin et al).

In the manufacture of HBCD, it is beneficial to provide solid HBCD particles in forms which are easily recoverable through the separation techniques used. For example, larger particle sizes such as that provided by agglomerization or crystal growth will be more readily recoverable by these techniques and therefore result in a larger yield. Such methods are disclosed, for example in U.K. No. 2,205,830 (Hermolin et al)
D.E. No. 3,120,621 (Jenkner et al)
U.S. No. 3,652,688 (Dlechowski et al)
U.S. No. 3,833,675 (Newcombe et al)

There continues to be a need for methods directed to producing HBCD particles with reduced residual bromides and other contaminants and with enhanced filterability.

SUMMARY

Improved methods have been discovered for purifying and agglomerating HBCD-containing particles. The methods comprise forming an aqueous admixture of HBCD particles and heating the admixture sufficiently to cause agglomerization of at least some of the particles into agglomerates larger than the original individual particles. These methods can provide improved purification of the HBCD particles and additionally provide enhancement of the separability of these particles from liquid compositions containing such particles.

DESCRIPTION OF THE PREFERRED EMBODIMENTS

Embodiments of the present invention consist of methods for obtaining a product from compositions comprising the components of (i) solid particles comprising HBCD;
(ii) liquid organic components, i.e. solvents; and
(iii) contaminants comprising one or more members of a group consisting of dodecyl bromides, hydrogen bromide, alkyl bromides and bromine.

According to one embodiment of the present invention, there is provided a method for obtaining an improved product from such a composition, this method comprising (1) forming an admixture of the above-said composition and water;

(2) heating this admixture for a time at a temperature and a pressure sufficient to remove at least a portion of the liquid organic components from this admixture and to form agglomerates with at least a portion of the solid particles; and (3) recovering from the admixture a product comprising the particles and the agglomerates;

wherein the forming and the heating are effective to enhance the removal of at least a portion of one or more of the members of the group of contaminants during this heating and/or recovering so as to reduce the concentration of the members of contaminants in the product.

The composition involved in this embodiment can be a typical reaction product obtained from the bromination of cyclododecatriene in nearly stoichiometric amounts in solvents to produce HBCD product. Illustrative of such bromination of cyclododecatriene are U.K. 2,205,830 (Hermolin et al) and U.S. Pat. No. 3,558,727 (Jenkner et al), incorporated in their entirety herein by reference. This HBCD product can have use as a flame retardant among other uses. The reaction produces a reaction product mass containing HBCD but site reaction can also produce unwanted by-products, e.g. allylic bromination, dehydrobromination and bromination of the solvent. Additional components which can act as contaminants to the product can also be present in the reaction mass, for example hydrogen bromide and residual bromine. The bromination reaction produces "HBCD particles" (i.e. "hexabromocyclododecane particles"), being solid particles which are predominantly HBCD. The liquid components of this reaction mass can be separated from the solids, such as by filtering to produce a residue which is predominantly the solid particles with some liquid components remaining associated with the solid particles. Other separation techniques, such as centrifugation or decantation, can also be used to produce a composition which is predominantly solid particles with some liquid composition remaining in association. A wetcake in accordance with this embodiment is preferably one which is predominantly HBCD particles, i.e. from about 55 to 95 weight percent. It is to be understood that the term "wetcake" can encompass forms of a separated mass from the reaction mass other than that obtained by filtration, provided that such separated mass is predominantly solid particles with some liquid associated with it, the amount of liquid being associated varying in accordance with the separation technique used. For example, decantation can produce a separated mass which is predominantly solid particles but containing more liquid than a filtered wetcake and the form of the separated mass can be a less compacted composition than that obtained in a filtered wetcake. Preferably, the wetcake can be convieniently admixed with water and dispersed therein.

A second component of the wetcake is solvent used in the bromination reaction. The solvent can be a single solvent or a mixture of several solvents used in the bromination reaction. Illustrative of such solvents are those found in U.S. Pat. No. 3,833,675 (e.g. lower alkyl esters, lower alkyl ethers, and lower alkyl nitriles); U.S. Pat. No. 3,652,688 (e.g. halogenated and halogen polar solvents); and U.S. Pat. No. 3,558,727 (e.g. lower alkyl alcohols), the term "lower alkyl" as used herein from these patents meaning $C_1$–$C_6$ linear or branched alkyl groups. These United States patents are incorporated herein by reference. Preferred solvents are $C_1$–$C_4$ alcohols; $C_1$–$C_4$ alkyl halides having one or more halogens in which the halogen is bromine, chlorine or both bromine and chlorine as substituents on the same alkyl group but not necessarily the same carbon atom; or a mixture of such alcohols and alkyl halides. Most preferably, the solvents used in this embodiment of the present invention include t-butyl alcohol, ethanol, n-propanol, isopropanol, n-butanol, methanol, 2-methyl propanol-1, butanol-2, carbon tetrachloride, chloroform, isobutyl bromide and dibromomethane. Solvents may also be present as residual washing agents used to wash the solid particles to remove solvent soluble contaminants.

In addition to solvent, other components are present, depending upon the methods of producing the wetcake and treatment thereof. For instance, the wetcake can be the product produced by the bromination of cyclododecatriene in the presence of an excess of bromine, resulting in the presence of bromine in the wetcake but not the presence of cyclododecatriene. Conversely, an excess of cyclododecatriene in the reaction can result in the presence of cyclododecatriene in the wetcake but the absence of bromine. Likewise, rinsing of the wetcake can result in the removal of some components, i.e. solvent rinse to remove solvent-soluble components. Also present in the wetcake can be dodecyl halides, hydrogen bromide, alkyl bromides or other water soluble brominated organics.

The admixture of this embodiment can be formed by adding wetcake to water, adding water to wetcake, or simultaneous admixture of wetcake and water together. Agitation can be performed to obtain a relatively homogeneous dispersion of solids in this admixture, the amount of agitation being dependent in part upon the initial form of the wetcake including such factors as the degree of compaction of the solid particles. This agitated admixture can be in the form of a watery suspension (i.e. slurry) susceptible to filtration. The weight ratio of water to wetcake in the admixture, preferably as a slurry, can vary over a range of about 99/1 to about 30/70 (water/wetcake). Preferably the water/wetcake weight ratio is at least about 1/1. The water admixed with the wetcake can be neutral, i.e. about pH 7 or range in pH from about 6 to about 10. A slightly basic water, preferably about 8 to about 9 pH, can provide the benefit of neutralization of the admixture, that is, reaction between the neutralizing agent, as discussed hereinbelow, and hydrogen bromide, residual bromine and other bromides to remove them.

Heating of the admixture can be performed by direct or indirect heat transfer methods, such as by hot gas or liquid injection directly into the admixture or by radiant or conductive heating of the admixture vessel for indirect heating. It is preferred that the hot gases be nonreactive with HBCD. Such hot gases include steam, nitrogen and ammonia, which ammonia can also provide a neutralization function. The most preferred hot gas is steam. Heating of the admixture can effect the removal of at least a portion, preferably substantially all, of residual solvent and bromide. Solvents with relatively lower boiling points may be removed by heating to a lower temperature than that used for the relatively higher boiling point solvents. A preferred solvent mixture of isobutyl alcohol and chloroform need be heated to a temperature of about 60 to about 100° C. If agglomeration is to be performed at a temperature higher than the boiling point of the system, pressurization can be performed to attain the temperature. Pressures which can be used are those consistent with the production of HBCD, preferably about 0.01 atmospheres to about 10 atmosphere, more preferably about 0.05 atmospheres to about 2.0 atmospheres; most preferably about ambient pressure. Pressures, temperatures and heating time spans should not be such as to damage the heat-sensitive HBCD product, e.g. dehydrobromination. When heating the admixture in accordance with the present invention, agglomeration of the solid particles will occur, forming agglomerates larger than the initial, pre-treatment size of the individual solid particles. Heating should be performed so as to preferably produce an average agglomerate size of at least about 100 microns, more preferably an average size of at least about 140 microns. Larger agglomerate sizes may also result from the process (i.e. 500 microns). Agglomeration of the particles results in an enhanced capability of separation of the HBCD product from the wetcake composition existing prior to the forming and heating process. This enhancement is present through use of separation techniques which rely at least in part upon particle size for effectiveness, such as filtration and centrifugation. Additionally, the agglomerates will have a heavier mass than the individual particles and therefore separation techniques which rely at least in part upon the relative mass of the treated material will also be enhanced, such as centrifugation and decantation.

Forming and heating in accordance with the present invention provides a means for the enhanced removal of at least a portion of the contaminants present in this admixture produced from the wetcake. For example, water washing a centrifuge cake to remove water soluble bromides can be difficult since the rinse water must first penetrate the coating of solvent and other contaminants on the HBCD containing particles. The present invention provides enhanced removal of solvent from the solid particles, thereby permitting better access of washing fluids to the solid particles, which washing fluid can better then flush or dissolve the water soluble contaminants associated with the solid particles. The present invention therefore provides a method which yields a consistently low water soluble bromide content compared to that in the prior art inasmuch as the prior methods could not consistently produce removal of the contaminants to the level obtained in accordance with the present invention. The present methods can produce a product having a consistently low water soluble bromide content generally below about 1000 ppm bromide, more frequently below about 200 ppm bromide.

The presence of water in the admixture (e.g. slurry) can provide an advantage in that water forms an azeotrope with many of the solvents used in HBCD production. Many of these azeotropes can have boiling points below that of the individual components, which can provide an economic advantage in reduced energy requirements for boiling off solvents. Azeotropic formation, e.g. binary, ternary and higher systems, has the further advantage in that solvent selection is broadened. For example, use of a higher alcohol as the sole solvent, such as 2-ethyl hexanol with a boiling point of 185° C., would not heretofore be favored. With heating (e.g. distillation), of an aqueous slurry containing 2-ethyl hexanol, an azeotrope of water and 2-ethyl hexanol with a boiling point of 99.1° C. is attained. Also, the use of azeotropic distillation can be effected with multiple solvent systems which have a combination of an azeotrope-forming solvent and a non-azeotrope-forming solvent.

As discussed hereinabove, the reaction product mass for HBCD production can contain "acidity", e.g. bromine and water soluble bromides such as hydrogen bromide. Removal of these contaminants can be effected, at least in part, through their reaction (i.e. "neutralization") with "neutralizing agents." The present invention can optionally incorporate this neutralization procedure as shown in another embodiment, in which the invention comprises, in combination, the following procedures:

(a) forming an HBCD wetcake admixture with wetcake and water;
(b) heating the HBCD wetcake admixture to effect agglomerization; and
(c) neutralizing acidity associated with the HBCD.

The admixture can be a slurry. Preferably the procedures of (b) heating and (c) neutralizing would be performed in conjunction such that some overlapping of the procedures would occur. More preferably, neutralization substantially commences with or after the start of heating and substantially ceases prior to or with cessation of heating. Heating is preferably performed by injection of steam into the slurry, such as in steam stripping or steam distillation.

Example of a preferred neutralization is the admixture of dilute aqueous sodium hydroxide (e.g. 5% or less sodium hydroxide) to react with hydrogen bromide to form water and sodium bromide, which dissolves in the water. In addition to dilute aqueous sodium hydroxide, neutralizing agents include aqueous or solid forms (preferably dilute) of amines, ammonia, ammonium hydroxide, calcium carbonate, potassium carbonate, potassium bicarbonate, sodium carbonate, sodium bicarbonate or combinations or mixtures thereof. Additionally, gaseous neutralizing agents, such as gaseous ammonia, can be used.

Other embodiments of the present invention include additional procedures of purification, e.g., filtration, centrifugation, evaporation, drying or other gas/liquid/solid separation. In accordance with one such embodiment, the invention is the method comprising the following procedures:

(a) forming a wetcake slurry with wetcake and water;
(b) neutralizing acidity associated with the solid particles in the slurry;
(c) steam distilling the slurry;
(d) separating solid particles from at least a portion of the slurry; and
(e) washing the solid particles.

The forming of a wetcake slurry, step (a), and the neutralization of such slurry, step (b), have already been discussed (see the earlier discussed embodiments).

Procedures (a), (b), (c), (d) and (e) need not be strictly performed in the sequence presented. The option of the substantially simultaneous practice of procedures (b) and (c), as well as that of procedures (d) and (e), is within this embodiment. Prior to the practice of these procedures, either separately or in combination, a washing step of the solid particles can be performed in conjunction with a separation step, both steps occurring prior to procedures (a) and (b).

Illustrative of one sequence of steps in accordance with this embodiment is the following:

Step 1 —brominate cyclododecatriene in solvent to form a reaction mass containing HBCD.

Step 2 —filter the reaction mass to produce a first filtrate.

Step 3 —wash (or rinse) the filtrate with a wash solution which comprises solvent (e.g. alcohol and halogenated hydrocarbon, such as isobutyl alcohol and chloroform for example) capable of reducing in the solids undesired contaminants, such as partially brominated cyclododecatriene, which could adversely affect the HBCD product by lowering melting point or causing discoloration. The solvent used to wash the filtrate can be fresh solvent of the same composition as the reaction solvent. Washing can be performed with the filtrate still on the filter (e.g. rinsing) or can be performed by slurrying the filtrate with the wash solution followed by a subsequent filtration to produce a washed filtrate. The temperature of the wash (or rinse) solution can be the same temperature as the final reaction mass temperature, preferably below about 60° C.

Step 4 —mix the filtrate with water and heat to cause the desired agglomeration, as well as optionally performing neutralization, by performing procedures (a) through (c), separately, simultaneously or in combination, such as, for example, in schemes I, II or III shown below:

| I | II | III |
|---|---|---|
| first (a) | first (a) and (b) together | first (a) |
| then (b) | then (c) | then (b) and (c) together |
| then (c) | | |

During this step 4, the make-up of the liquid phase of the slurry can change due to the evaporation of solvent and possibly the condensation of water. After removal of from at least some to substantially all of the solvent, continued heating of the slurry can be performed to drive off water. A simpler, more cost effective method to remove the remaining water can be to perform a filtration of the slurry, as in the next step.

Step 5 —separate solid particles from the slurry. This can be performed by filtration to produce a second filtrate.

Step 6 —wash (or rinse) the filtrate with a water wash solution to remove sodium bromides and other unwanted water-soluble contaminants formed in upstream reactions (i.e. the reaction used in the preparation of HBCD). This can optionally be performed either on the second filtrate during step 5 or by slurrying the second filtrate with wash water and re-filtering to produce an HBCD product ready for drying.

This sequence of steps results in the removal of unwanted solvent-soluble contaminants before the steam distillation and neutralization (procedures b and c). Steam distillation can then be performed to remove residual reaction solvent and wash solvent from the solid particles. Removal of unwanted water-soluble contaminants can be deferred until after removal of solvent, which solvent could interfere with water washing if present.

A water wash in the upstream filtration operations (i.e. step 2) would be neither efficient nor consistent in the results obtained, because contaminants, such as the solvents or by-products, associated with the solids would interfere with the contact between water and bromides. This embodiment (step 4 solvent removal and step 6 water wash) produces a consistent reduction of water soluble bromides which is reproducible and produces a concentration of soluble bromide in the product much lower in comparison with prior art techniques. Without the water wash of step 6, products can be produced with an improved water soluble bromide content of at or less then about 1000 ppm; however, with the water wash of step 6, even lower consistent levels of water soluble bromide content can be obtained, at or below about 200 ppm, preferably about 50 ppm. These levels (e.g. about 1000 ppm, 200 ppm and 50 ppm respectively) can be obtained optionally without the step 2 solvent rinse.

This sequence of filtration-solvent wash followed by distillation-neutralization followed by filtration-water wash produces several advantages. For slurries with components which have boiling points higher than that of water, e.g. isobutanol or isobutyl bromide, removal of these components before the drying step allows a lower temperature to be used during the drying operation, which is beneficial to the heat sensitive hexabromocyclododecane product. Additionally, with little or no organic derivatives or solvents removal in the dryer operations, the requirement to protect against environmentally damaging emissions during drying operations can be reduced.

The following example illustrates one embodiment of the invention, but is not intended to limit the invention to a particular set of parameters.

EXAMPLE A

A solvent mixture was made by admixing equal weights of chloroform and isobutyl alcohol. CDT and bromine (about 1 mole CDT/3.15 moles bromine) were reacted in the solvent mixture to produce an HBCD-containing mass. Reaction was at atmospheric pressure and the temperature of the reaction mass was not permitted to rise above 45° C. Reaction temperature was maintained for thirty minutes after which ten (10) pounds of water per pound of solvent and about one and three-quarters ($1\frac{3}{4}$) moles of sodium carbonate ($Na_2CO_3$) per mole of by-product hydrogen bromide (HBr) were added to the reaction to neutralize the reaction mass. The mixture was allowed to stand for about two (2) hours, after which two samples, Sample 1 and Sample 2, were removed from the reaction mass and water, approximately one pound of water per pound of HBCD, was added to each sample. The samples exhibited two phases: a clear aqueous phase and a gummy mixture of a solid phase and solvent phase, resulting from mixing HBCD with cold water. The two samples were then treated in the following manner to change the gummy solid phase to a dried solid state to permit comparative analysis to show advantages of the present invention.

Sample A-1: Sample 1 was decanted to drain substantially all of the aqueous phase from the sample, leaving behind the gummy mixture which was still wet with some retained amount of the solvent phase. This gummy solids phase was dried overnight in a vacuum oven at about 80° C. and about 33 mm Hg. Analysis of the dried material for residual bromide was then performed.

Sample A-2: Sample 2 was placed in a container and heated to a temperature of 98° C., which was sufficient to vaporize solvent from the sample. The sample was heated about 30 minutes at about 98° C. to eliminate the odor of solvents in the emitted vapors. The absence of solvent odor indicated that essentially all volatile solvent had been driven off from the sample. The gum in the sample had been converted into discrete particles of solids. Filtration was performed to recover the discrete solids, which were then washed with fresh tap water and dried in a vacuum oven at about 80° C. and about 33 mm in Hg to yield dried solids.

Comparison: Analysis of the dried solids from Sample A and Sample A-2 was performed:

| Sample | Residual Bromide, ppm |
| --- | --- |
| A-1 | 980 |
| A-2 | 160 |

The following example illustrates one embodiment in which agglomeration is caused by distillation, but is not intended to limit the invention to a particular set of parameters.

EXAMPLE B

Sample B-1: A solvent mixture was made by admixing 128 grams of chloroform and 32 grams of isobutanol. A reaction mass was made by feeding 50 grams of CDT and 150 grams of bromine into the solvent over a 55 minutes period. The temperature of the reaction mass rose to 60° C. and was held at that temperature until 45 minutes after the completion of the addition of CDT and bromine. The reaction mass was then cooled to 15° C. and held for 30 minutes. A portion (Sample B-1-Median-Before) of the solution was drawn off for microtrac particle size analysis. The remaining sample was filtered, which included use of an additional 75 grams of solvent mixture (60 grams chloroform/15 grams isobutanol), and then washed with 250 grams of hot water, yielding a wet cake of 139 grams. The next day the wet cake was slurried in 350 milliliters of water (pH=6) and heated with 1.5 grams of Dow anionic surfactant to an overhead temperature of 100° C. The reaction produced about 80 milliliters of distillate. A portion (Sample B-1-Median-After) of the slurry was drawn off for microtrac particle size analysis. Testing of the supernatant with methylene chloride showed only a trace of isobutanol.

Sample B-2: A solvent mixture was made by admixing 30 grams of chloroform and 30 grams of isobutanol. A reaction mass was made by feeding 50 grams of CDT dissolved in 100 grams of solvent mixture (50 grams chloroform/50 grams isobutanol) and 154 grams of bromine into the solvent over a 70 minutes period. The temperature of the reaction mass rose to 45° C. and was held at that temperature until 25 minutes after the completion of the addition of CDT and bromine. The reaction mass was then cooled to 15° C. and held for 5 minutes. A portion (Sample B-2-Median-Before) of the solution was drawn off for microtrac particle size analysis. The remaining sample was filtered and then washed with 250 milliliters of hot water, yielding a wet cake of 203 grams. The next day the wet cake was slurried in 350 milliliters of water (pH=3), neutralized with 0.8 grams of sodium carbonate and heated with 1.5 grams of Dow anionic surfactant to an overhead temperature of 100° C. The reaction produced about 100 milliliters of distillate. A portion (Sample B-2-Median-After) of the slurry was drawn off for microtrac particle size analysis.

The tabulated values below are HBCD average particle sizes in microns before and after distillation, as obtained from the foregoing Samples B-1 and B-2:

| Sample | Median-Before | Median-After |
| --- | --- | --- |
| B-1 | 22 | 144 |
| B-2 | 22 | 154 |

What is claimed is:

1. A method for obtaining an improved product from a composition, said composition comprising:
   (i) solid particles comprising hexabromocyclododecane;
   (ii) a solvent or mixture of solvents used in the production of hexabromocyclododecane; and
   (iii) one or more members selected from the group consisting essentially of dodecyl bromides, hydrogen bromide, lower alkyl bromides and bromine;
said method comprising
   (1) forming an admixture of said composition and water;
   (2) heating said admixture for a time and at a temperature and a pressure, which time, temperature and pressure are sufficient to remove at least a portion of said solvent from said admixture and to form agglomerates with at least a portion of said particles; and
   (3) recovering from said admixture a product comprising said particles and agglomerates;
wherein said forming and said heating are effective to enhance the removal of at least a portion of said solvent and/or said one or more members so as to obtain said improved product.

2. The method of claim 1 wherein said solvent comprises at least one $C_1$-$C_4$ alcohols, at least one $C_1$-$C_4$ alkyl halides, or mixture thereof.

3. The method of claim 2 wherein the $C_1$-$C_4$ alcohol is isobutyl and the $C_1$-$C_4$ alkyl halide is chloroform.

4. The method of claim 1 wherein said composition is a wetcake and the weight ratio of said water/said wetcake is from about 99/1 to about 30/70, said wetcake being about 75 percent to 95 percent HBCD particles.

5. The method of claim 1 wherein said water/wetcake weight ratio is at least about 1/1.

6. The method of claim 1 wherein the pH of said water is about 8 to about 9.

7. The method of claim 1 wherein heating is effected by injection of hot ammonia, nitrogen or steam.

8. The method of claim 1 wherein the average size of said agglomerates in said product is at least about 100 microns.

9. The method of claim 1 wherein said method is effective to produce a residual bromide content below 1000 ppm in said product.

10. A method for producing a hexabromocyclododecane product, said method comprising
   (1) forming a slurry with water and wetcake, said wetcake being predominant in particles comprising hexabromocyclododecane, and said wetcake having been formed by filtering a composition to obtain a first filtrate and rinsing said first filtrate with a solvent comprising isobutyl alcohol and chloroform;
   (2) steam heating said slurry at about ambient pressure and at a temperature of about 60° C. to about 100° C. for a time sufficient to effect agglomeration of at least some of said particles and to effect removal of substantially all of said solvent from said slurry; and
   (3) filtering said slurry after steam heating to obtain a second filtrate and rinsing said second filtrate with water to form said hexabromocyclododecane product.

11. The method of claim 10 wherein said agglomeration produces an average agglomerates size of at least about 100 microns and a water soluble bromide content below about 1000 ppm in said product.

12. A method for agglomerating hexabromocyclododecane particles, said method comprising:
   (a) forming a slurry with water and wetcake which is predominate in said hexabromocyclododecane particles; and
   (b) heating said slurry to a temperature sufficient to effect said agglomerating.

13. The method of claim 12 wherein said wetcake comprises at least one $C_1$-$C_4$ alcohols, at least one $C_1$-$C_4$ alkyl halides, or mixtures thereof.

14. The method of claim 13 wherein heating is maintained until substantially all of said alcohols and said alkyl halides are removed from said slurry.

15. The method of claim 13 wherein the alcohol is isobutyl alcohol, the alkyl halide is chloroform and wherein the temperature of said slurry is about 60° to 100° C.

16. The method of claim 14 wherein said temperature is obtained by passing steam through said slurry.

17. The method of claim 12 wherein heating is performed by steam distillation.

18. The method of claim 17 wherein distilling is carried on sufficiently to obtain an average solid hexabromocyclododecane particle size of at least 100 microns.

19. The method of claim 12 wherein heating comprises use of hot ammonia, nitrogen or steam.

20. The method of claim 12 further comprising neutralization of acidity associated with said hexabromocyclododecane particles and wherein heating is by steam distillation.

21. The method of claim 20 wherein steam distillation follows neutralization.

22. The method of claim 20 wherein steam distillation and neutralization are performed at least in part simultaneously.

23. The method of claim 12 further comprising washing of said wetcake to effect removal of at least a portion of contaminants associated with said wetcake.

24. The method of claim 23 further comprising water washing said hexabromododecane particles after agglomerating, such that said particles after washing have a water soluble bromide content not exceeding about 200 ppm bromide.

* * * * *

UNITED STATES PATENT AND TRADEMARK OFFICE
CERTIFICATE OF CORRECTION

PATENT NO. : 5,004,847

DATED : April 2, 1991

INVENTOR(S) : Phillip R. Beaver, et al.

It is certified that error appears in the above-identified patent and that said Letters Patent is hereby corrected as shown below:

Column 9, line 30 reads "isobutyl" and should read -- isobutyl alcohol --.

Signed and Sealed this

Eighth Day of December, 1992

Attest:

DOUGLAS B. COMER

Attesting Officer

Acting Commissioner of Patents and Trademarks